US009591233B2

(12) United States Patent
Adachi

(10) Patent No.: US 9,591,233 B2
(45) Date of Patent: Mar. 7, 2017

(54) IMAGING DEVICE, ENDOSCOPE, ENDOSCOPE SYSTEM, AND METHOD FOR DRIVING IMAGING DEVICE

(71) Applicant: OLYMPUS CORPORATION, Tokyo (JP)

(72) Inventor: Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/989,094

(22) Filed: Jan. 6, 2016

(65) Prior Publication Data
US 2016/0119528 A1    Apr. 28, 2016

Related U.S. Application Data

(63) Continuation of application No. PCT/JP2015/056833, filed on Mar. 9, 2015.

(30) Foreign Application Priority Data

Aug. 21, 2014    (JP) ................. 2014-168510

(51) Int. Cl.
*H04N 5/235*    (2006.01)
*A61B 1/04*    (2006.01)
(Continued)

(52) U.S. Cl.
CPC ....... *H04N 5/2354* (2013.01); *A61B 1/00006* (2013.01); *A61B 1/00009* (2013.01);
(Continued)

(58) Field of Classification Search
CPC ....... H04N 5/2354; H04N 5/378; A61B 1/045
See application file for complete search history.

(56) References Cited

U.S. PATENT DOCUMENTS

| 8,487,986 B2 | 7/2013 | Hashimoto et al. |
| 2006/0020168 A1* | 1/2006 | Naruse ............... A61B 1/00027 600/179 |
| 2009/0303319 A1* | 12/2009 | Sato .................. A61B 1/00158 348/65 |

FOREIGN PATENT DOCUMENTS

| JP | H05-191416 A | 7/1993 |
| JP | 2005-229292 A | 8/2005 |
| WO | WO 2012/020709 A1 | 2/2012 |

OTHER PUBLICATIONS

Japanese Office Action dated Sep. 24, 2015 issued in JP 2015-531379.

* cited by examiner

*Primary Examiner* — Zhubing Ren
(74) *Attorney, Agent, or Firm* — Scully, Scott, Murphy & Presser, P.C.

(57) ABSTRACT

An imaging device includes: an image sensor including pixels and configured to receive light from outside, and generate and output an imaging signal according to an amount of the received light; a transmission cable connected to the image sensor and configured to propagate the imaging signal; a terminating resistor provided at a terminal of the transmission cable, the terminal resistor including an alternating current terminating resistor with variable resistance and a direct current terminating resistor with variable resistance, and having a constant combined resistance of the direct current terminating resistor and the alternating current terminating resistor; and a control unit configured to perform control to make a resistance of the direct current terminating resistor during a blanking period in which the image sensor does not output the imaging signal higher than that during a normal operation period in which the image sensor outputs the imaging signal.

6 Claims, 8 Drawing Sheets

(51) Int. Cl.
    *H04N 5/225*     (2006.01)
    *H04N 5/378*     (2011.01)
    *A61B 1/00*     (2006.01)
    *H04N 7/18*     (2006.01)
    *A61B 1/045*     (2006.01)

(52) U.S. Cl.
    CPC ............ *A61B 1/00114* (2013.01); *A61B 1/04* (2013.01); *A61B 1/045* (2013.01); *H04N 5/225* (2013.01); *H04N 5/378* (2013.01); *H04N 7/183* (2013.01); *H04N 2005/2255* (2013.01)

| | FIRST SWITCH | SECOND SWITCH | DC TERMINATING RESISTOR | AC TERMINATING RESISTOR |
|---|---|---|---|---|
| NORMAL OPERATION PERIOD | ON | OFF | 100Ω | 100Ω |
| BLANKING PERIOD | OFF | ON | 200Ω | 67Ω |

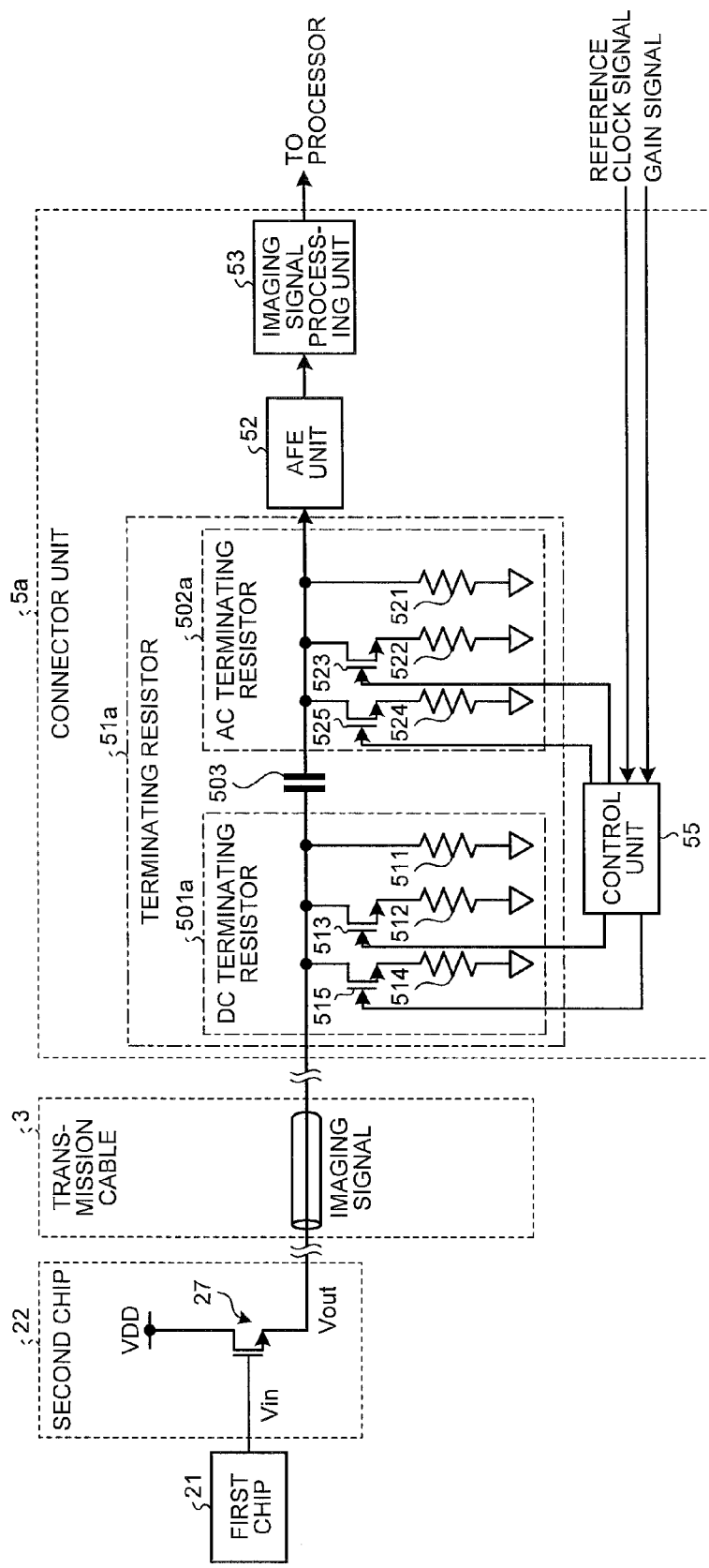

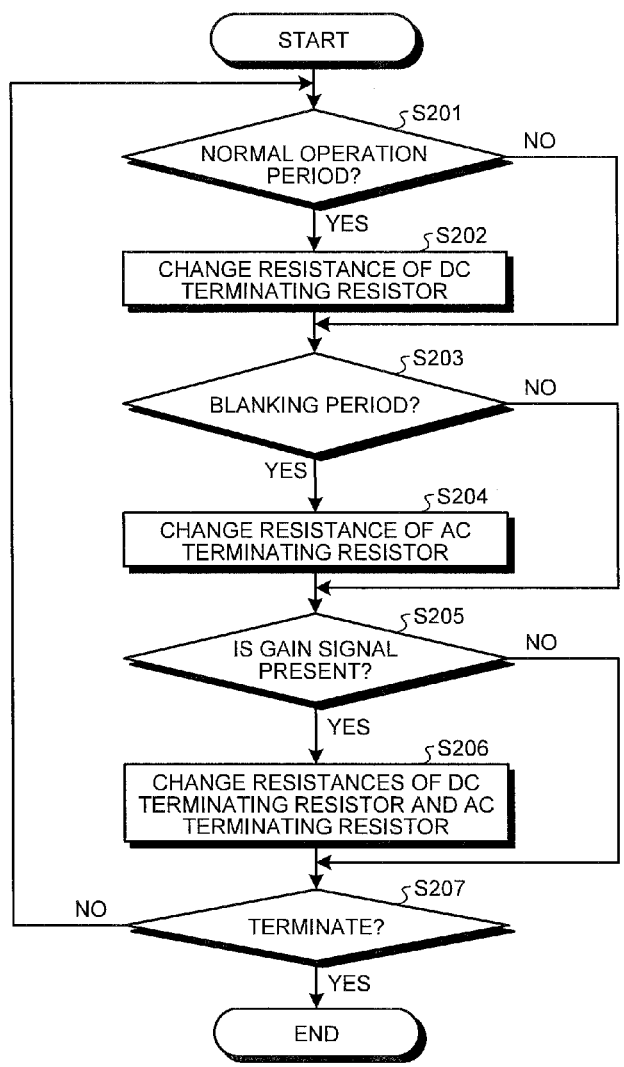

IMAGING DEVICE, ENDOSCOPE, ENDOSCOPE SYSTEM, AND METHOD FOR DRIVING IMAGING DEVICE

CROSS-REFERENCE TO RELATED APPLICATIONS

This application is a continuation of PCT international application Ser. No. PCT/JP2015/056833 filed on Mar. 9, 2015 which designates the United States, incorporated herein by reference, and which claims the benefit of priority from Japanese Patent Applications No. 2014-168510, filed on Aug. 21, 2014, incorporated herein by reference.

BACKGROUND OF THE INVENTION

1. Field of the Invention

The present invention relates to an imaging device that images a subject and generates image data of the subject, an endoscope, an endoscope system, and a method for driving an imaging device.

2. Description of the Related Art

In related art, for endoscopes including image sensors such as CCDs (charge coupled devices) or CMOSs (complementary metal oxide semiconductors), a technology for compensating for variations in transmission cables by matching impedances of transmission cables for transmitting signals from processors to image sensors has been known (refer to WO 2012/020709). With this technology, signal voltage of an image sensor is output to the outside via an amplifier circuit such as a source follower circuit, a variable resistor is provided at a terminal of a transmission cable for transmitting a signal from the image sensor, and the resistance of the variable resistor is changed for impedance matching of the transmission cable.

In the aforementioned WO 2012/020709, however, because the load of the terminating resistor of the transmission cable is driven by the source follower circuit, current flows through the transmission even during a blanking period in which no imaging signal is transmitted, which disadvantageously results in large power consumption.

There is a need for an imaging device, an endoscope, an endoscope system, and a method for driving an imaging device capable of reducing power consumption.

SUMMARY OF THE INVENTION

An imaging device according to one aspect of the present invention includes: an image sensor including a plurality of pixels arranged in a two-dimensional matrix and configured to receive light from outside, and generate and output an imaging signal according to an amount of the received light; a transmission cable connected to the image sensor and configured to propagate the imaging signal; a terminating resistor provided at a terminal of the transmission cable, the terminal resistor including an alternating current terminating resistor with variable resistance and a direct current terminating resistor with variable resistance, and having a constant combined resistance of the direct current terminating resistor and the alternating current terminating resistor; and a control unit configured to perform control to make a resistance of the direct current terminating resistor during a blanking period in which the image sensor does not output the imaging signal higher than that during a normal operation period in which the image sensor outputs the imaging signal.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a circuit diagram illustrating a detailed configuration of a second chip and a configuration of a main part of a connector unit of an endoscope according to a second embodiment of the present invention;

FIG. 7 is a table relating to a driving timing of each of a first switch and a third switch of a DC terminating resistor and a second switch and a fourth switch of an AC terminating resistor illustrated in FIG. 6 and a combined resistance of each of the DC terminating resistor and the AC terminating resistor;

FIG. 8 is a flowchart illustrating an outline of processing performed by the endoscope according to the second embodiment of the present invention;

DETAILED DESCRIPTION OF THE PREFERRED EMBODIMENTS

Figure 1:
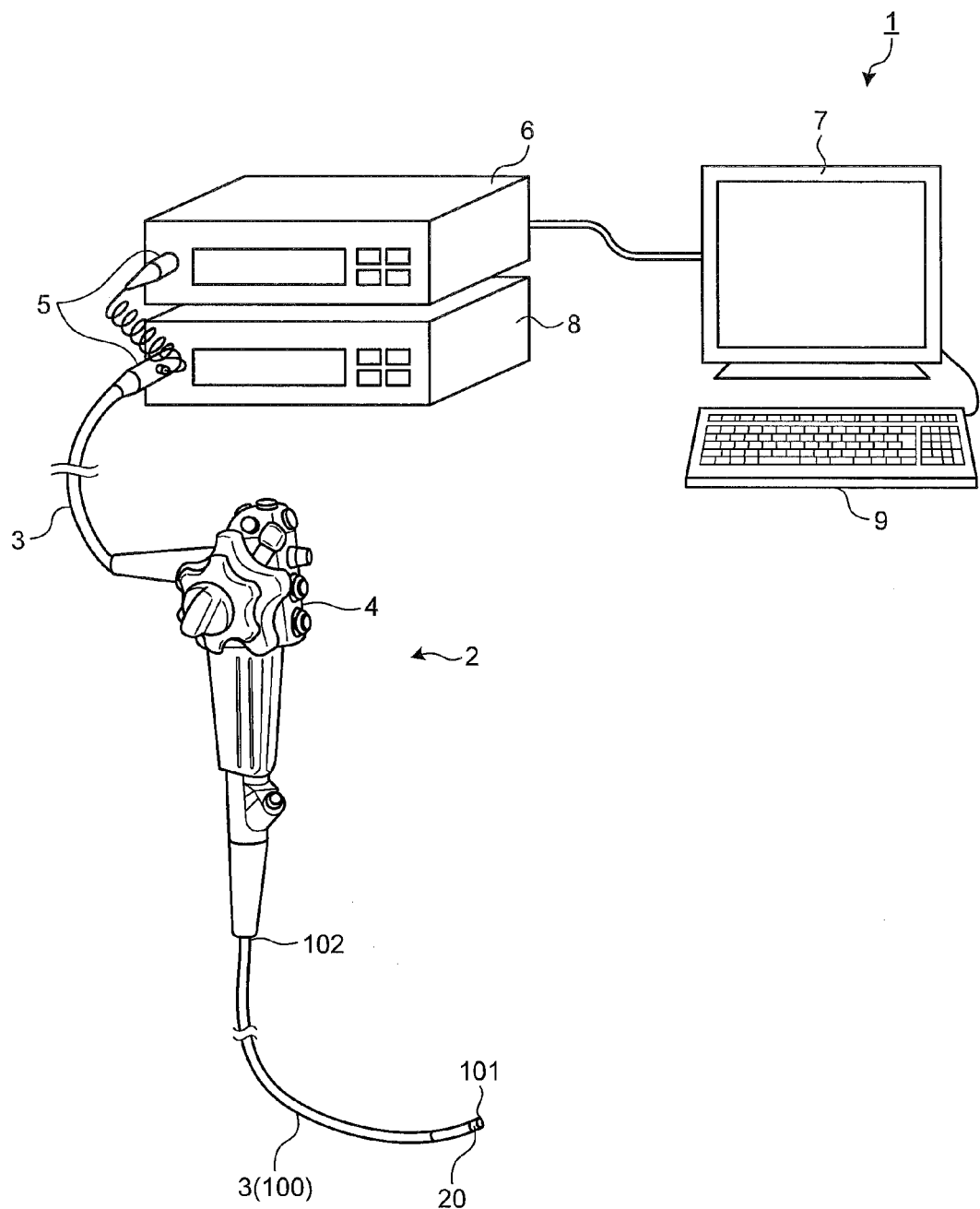
FIG. 1 is a view schematically illustrating an overall configuration of an endoscope system according to a first embodiment of the present invention.

Hereinafter, an endoscope system including an imaging device, which is a mode for carrying out the present invention (hereinafter referred to as an "embodiment"), will be described. The present invention is not limited to the embodiment. In depiction of the drawings, the same components will be designated by the same reference numerals. Furthermore, note that the drawings are schematic, and that the relations between the thicknesses and the widths of respective members, the ratios of the members and the like may be different from the actual relations, ratios, and the like. Furthermore, a drawing may also include parts with dimensions and ratios different from those of another drawing.

First Embodiment

Configuration of Endoscope System

FIG. 1 is a view schematically illustrating an overall configuration of an endoscope system according to a first embodiment of the present invention. An endoscope system 1 illustrated in FIG. 1 includes an endoscope 2 (imaging device), a transmission cable 3, a connector unit 5, a processor 6 (processing device), a display device 7, light source device 8, and an input unit 9.

The endoscope 2 inserts an insertion part 100 that is a part of the transmission cable 3 into a body cavity of a subject to take an in-vivo image of the subject, and outputs a resulting imaging signal (image data) to the processor 6. In addition, the endoscope 2 is provided with an imaging unit 20 (imaging device) configured to take an in-vivo image on one end side of the transmission cable 3, that is, on a distal end 101 side of the insertion part 100 to be inserted into a body cavity of a subject, and connected with an operating unit 4 configured to receive various operations on the endoscope 2 on a proximal end 102 side of the insertion part 100. The imaging unit 20 is connected to the connector unit 5 by the transmission cable 3 via the operating unit 4. An imaging signal of an image taken by the imaging unit 20 passes through the transmission cable 3 having a length of several meters, for example, and is output to the connector unit 5. In the present embodiment, the endoscope 2 functions as an imaging device.

The transmission cable 3 connects the endoscope 2 and connector unit 5, and also connects the endoscope 2 and the light source device 8. The transmission cable 3 also propagates an imaging signal generated by the imaging unit 20 to the connector unit 5.

The connector unit 5 is connected with the endoscope 2, the processor 6, and the light source device 8, performs predetermined signal processing on an imaging signal output by the connected endoscope 2, converts the imaging signal from analog to digital (A/D conversion), and outputs the converted signal as an image signal to the processor 6.

The processor 6 performs predetermined image processing on an image signal output from the connector unit 5, and generally controls the whole endoscope system 1. In the present first embodiment, the processor 6 functions as a processing device.

The display device 7 displays an image corresponding to the image signal subjected to image processing by the processor 6. The display device 7 also displays various information data on the endoscope system 1. The display device 7 includes a display panel of liquid crystal, organic EL (electro luminescence), or the like.

The light source device 8 includes a halogen lamp or a white LED (light emitting diode), for example, and emits illumination light from the distal end of the insertion part 100 of the endoscope 2 toward a subject via the connector unit 5 and the transmission cable 3.

The input unit 9 includes a keyboard, a mouse, and the like, for example, and receives input of information on various operations of the endoscope system 1. For example, the input unit 9 receives input of an instruction signal indicating amplification (gain-up) of an imaging signal imaged by the endoscope 2 or a light intensity of the light source device 8.

Figure 2:
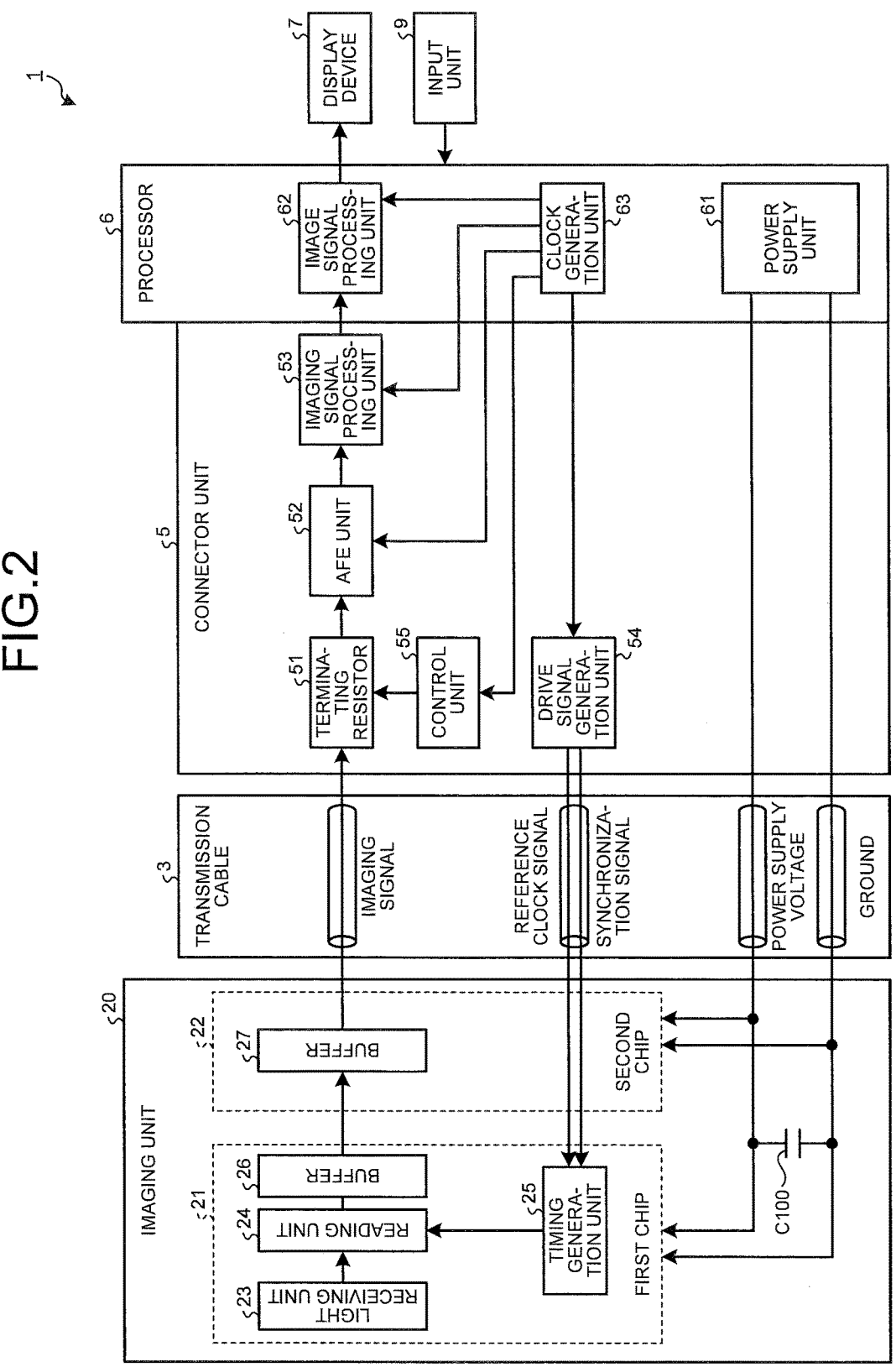
FIG. 2 is a block diagram illustrating functions of a main part of the endoscope system according to the first embodiment of the present invention.

FIG. 2 is a block diagram illustrating functions of a main part of the endoscope system 1. With reference to FIG. 2, details of configurations of the respective components of the endoscope system 1 and a path of an electrical signal in the endoscope system 1 will be described. As illustrated in FIG. 2, the imaging unit 20 includes a first chip 21 (image sensor) and a second chip 22.

The first chip 21 (image sensor) includes a light receiving unit 23 having a plurality of pixels arranged in a two-dimensional matrix and configured to generate and output an imaging signal according to the amount of light received, a reading unit 24 configured to read an imaging signal resulting from photoelectric conversion at the light receiving unit 23, a timing generation unit 25 configured to generate a timing signal on the basis of a reference clock signal and a synchronization signal input from the connector unit 5 and output the timing signal to the reading unit 24, and a buffer 26 configured to temporarily hold an imaging signal read by the reading unit 24 from the light receiving unit 23.

The second chip 22 includes a buffer 27 configured to output an imaging signal output from the first chip 21, that is, output from each of the pixels. A more detailed configuration of the second chip 22 will be described later with reference to FIG. 3.

The imaging unit 20 also receives a supply voltage (VDD) generated by a power supply unit 61 in the processor 6 via the transmission cable 3 together with a ground voltage (GND). A capacitor C100 for power supply stabilization is provided between the power supply voltage (VDD) and the ground voltage (GND) supplied to the imaging unit 20.

The connector unit 5 electrically connects the endoscope 2 (imaging unit 20) and the processor 6 with each other, and functions as a relay processor that relays an electrical signal. The connector unit 5 and the imaging unit 20 are connected to each other by the transmission cable 3, and the connector unit 5 and the processor 6 are connected to each other by a coil cable. The connector unit 5 is also connected to the light source device 8. The connector unit 5 includes a terminating resistor 51, an analog front end unit 52 (hereinafter referred to as an "AFE unit 52"), an imaging signal processing unit 53, a drive signal generation unit 54, and a control unit 55.

The terminating resistor 51 is provided at a terminal of the transmission cable 3, and has a plurality of resistors. The resistance of the terminating resistor 51 is changed under the control of the control unit 55. A more detailed configuration of the terminating resistor 51 will be described later with reference to FIG. 3

The AFE unit 52 receives an imaging signal transmitted from the imaging unit 20, performs impedance matching thereon by a passive element such as a resistor, and then extracts an alternating component by a capacitor, and determines an operating point by a voltage dividing resistor. The AFE unit 52 performs A/D conversion of an analog imaging signal transmitted from the imaging unit 20, and outputs a resulting digital imaging signal to the imaging signal processing unit 53.

The imaging signal processing unit 53 performs predetermined signal processing such as vertical line removal and noise reduction on a digital imaging signal input from the AFE unit 52, and outputs the processed signal to the processor 6. The imaging signal processing unit 53 includes a FPGA (field programmable gate array), for example.

The drive signal generation unit 54 generates a synchronization signal indicating a start position of each frame on the basis of a reference clock signal (a clock signal of 27 MHz, for example) that is supplied from the processor 6 and that is a reference of operations of the respective components of the endoscope 2, and outputs the synchronization signal together with the reference clock signal to the timing generation unit 25 of the imaging unit 20 via the transmission cable 3. Note that the synchronization signal generated by the drive signal generation unit 54 includes a horizontal synchronization signal and a vertical synchronization signal.

The control unit 55 includes a FPGA, for example. The control unit 55 performs control to change the resistance of the terminating resistor 51 so as to suppress current of the endoscope 2 during a blanking period of the imaging unit 20 on the basis of the reference clock signal that is supplied from the processor 6 and that is a reference of operations of the respective components of the endoscope 2. Specifically, the control unit 55 performs control to make the resistance of a direct current terminating resistor of the terminating resistor 51 during the blanking period during which the imaging unit 20 (image sensor) does not output an imaging signal higher than that during a normal operation period during which the imaging unit 20 (image sensor) outputs an imaging signal (hereinafter simply referred to as a "normal operation period") so as to suppress the current output by the imaging unit 20.

The processor 6 is a control device that generally controls the whole endoscope system 1. The processor 6 includes a power supply unit 61, an image signal processing unit 62, and a clock generation unit 63.

The power supply unit 61 generates a power supply voltage (VDD), and supplies the generated power supply voltage together with the ground voltage (GND) to the imaging unit 20 via the connector unit 5 and the transmission cable 3.

The image signal processing unit 62 performs image processing such as synchronization, white balance (WB) adjustment, gain adjustment, gamma correction, digital-to-analog (D/A) conversion, and format conversion on the digital imaging signal subjected to signal processing at the imaging signal processing unit 53 to convert the imaging signal to an image signal, and outputs the image signal to the display device 7.

The clock generation unit 63 generates a reference clock signal that is a reference of operations of the respective components of the endoscope system 1, and outputs the reference clock signal to the AFE unit 52, the imaging signal processing unit 53, the drive signal generation unit 54, and the control unit 55.

Configuration of Second Chip and Terminating Resistor

Figure 3:
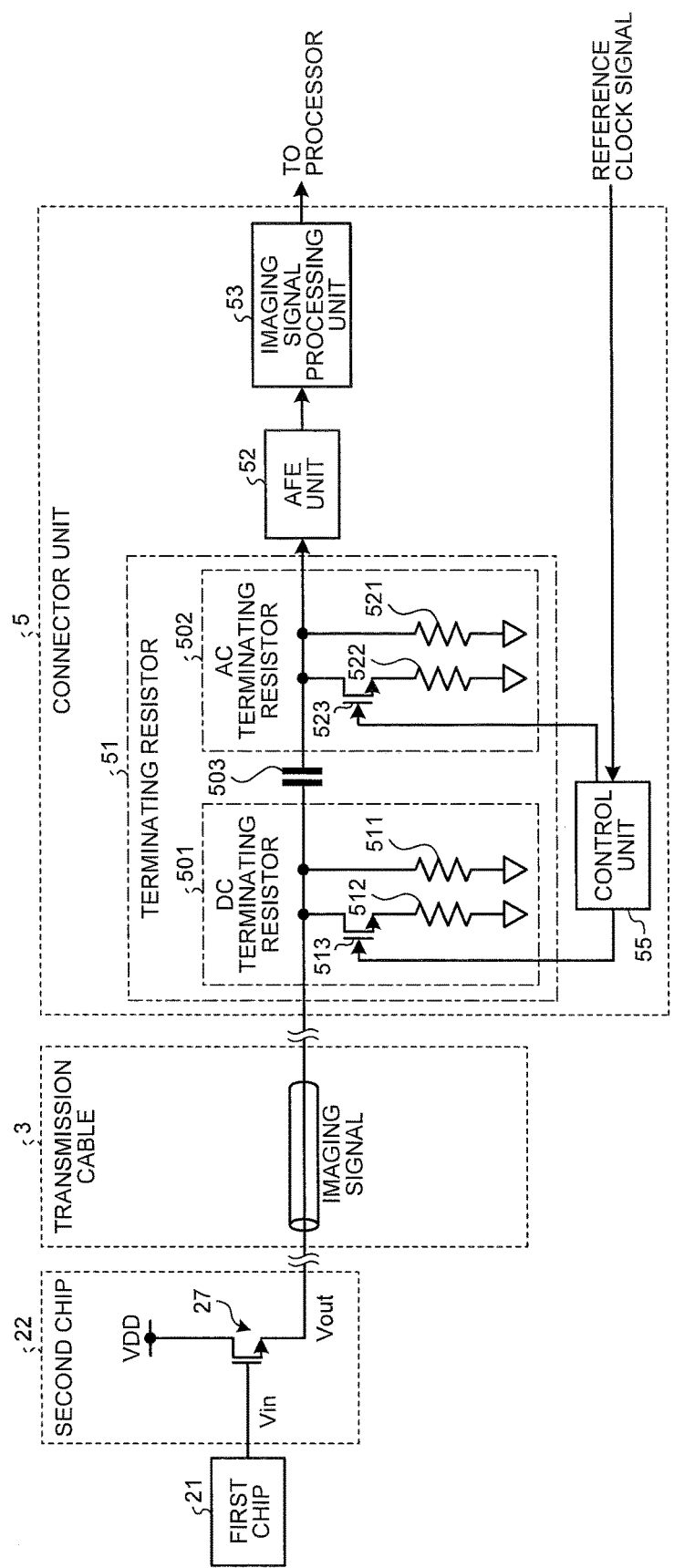
FIG. 3 is a circuit diagram illustrating a detailed configuration of a second chip and a configuration of a main part of a connector unit illustrated in FIG. 2.

Next, a detailed configuration of the second chip 22 and a detailed configuration of a main part of the connector unit 5 described above will be described. FIG. 3 is a circuit diagram illustrating a detailed configuration of the second chip 22 and a configuration of a main part of the connector unit 5 illustrated in FIG. 2. Although the characteristic impedance of the transmission cable 3 is 50Ω in the description below, the characteristic impedance can be changed as appropriate.

The buffer 27 of the second chip 22 includes a NMOS, and has one end (drain side) connected to the power supply voltage VDD, the other end (source side) connected to the transmission cable 3, and a gate to which a signal line for supplying an imaging signal (Vin) input from the first chip 21 is connected. The buffer 27 amplifies the imaging signal (Vin) input from the first chip 21, and outputs the amplified imaging signal to the transmission cable 3 (Vout).

The terminating resistor 51 of the connector unit 5 is provided at a terminal of the transmission cable 3, and includes a direct current terminating resistor 501 (hereinafter referred to as a "DC terminating resistor 501") with variable resistance and an alternating current terminating resistor 502 (hereinafter referred to as "AC terminating resistor 502") with variable resistance, and a DC blocking capacitor 503 that blocks a direct current component. The terminating resistor 51 has a constant combined resistance (50Ω) of the DC terminating resistor 501 and the AC terminating resistor 502.

The DC terminating resistor 501 includes a first resistor 511 and a second resistor 512 connected in parallel to the transmission cable 3, and a first switch 513 connected in series with the second resistor 512.

The first resistor 511 has one end connected to the transmission cable 3 and the other end connected to the ground. The first resistor 511 has a resistance of 200Ω.

The second resistor 512 has one end connected to the first switch 513 and the other end connected to the ground. The second resistor 512 has a resistance of 200Ω.

The first switch 513 includes a NMOS, has one end (drain side) connected to the transmission cable 3, the other side (source side) connected to the second resistor 512, and a gate to which a signal line for supplying a signal input from the control unit 55 is connected. The first switch 513 switches the resistance of the DC terminating resistor 501 under the control from the control unit 55. Specifically, when an ON signal is input from the control unit 55 (when a voltage is applied), the first switch 513 connects the first resistor 511 and the second resistor 512 in parallel.

The AC terminating resistor 502 includes a third resistor 521 and a fourth resistor 522 connected in parallel to the transmission cable 3, and a second switch 523 connected in series with the fourth resistor 522.

The third resistor 521 has one end connected to the transmission cable 3 and the other end connected to the ground. The third resistor 521 has a resistance of 100Ω.

The fourth resistor 522 has one end connected to the second switch 523 and the other end connected to the ground. The fourth resistor 522 has a resistance of 200Ω.

The second switch 523 includes a NMOS, and has one end (drain side) connected to the transmission cable 3, the other side (source side) connected to the fourth resistor 522, and a gate to which a signal line for supplying a signal input from the control unit 55 is connected. The second switch 523 switches the resistance of the AC terminating resistor 502 under the control from the control unit 55. Specifically, when an ON signal is input from the control unit 55 (when a voltage is applied), the second switch 523 connects the third resistor 521 and the fourth resistor 522 in parallel.

The thus configured terminating resistor 51 performs control to make the resistance of the DC terminating resistor 501 during the blanking period of the imaging unit 20 higher than that during the normal operation period under the control of the control unit 55.

Figures 4, 5:
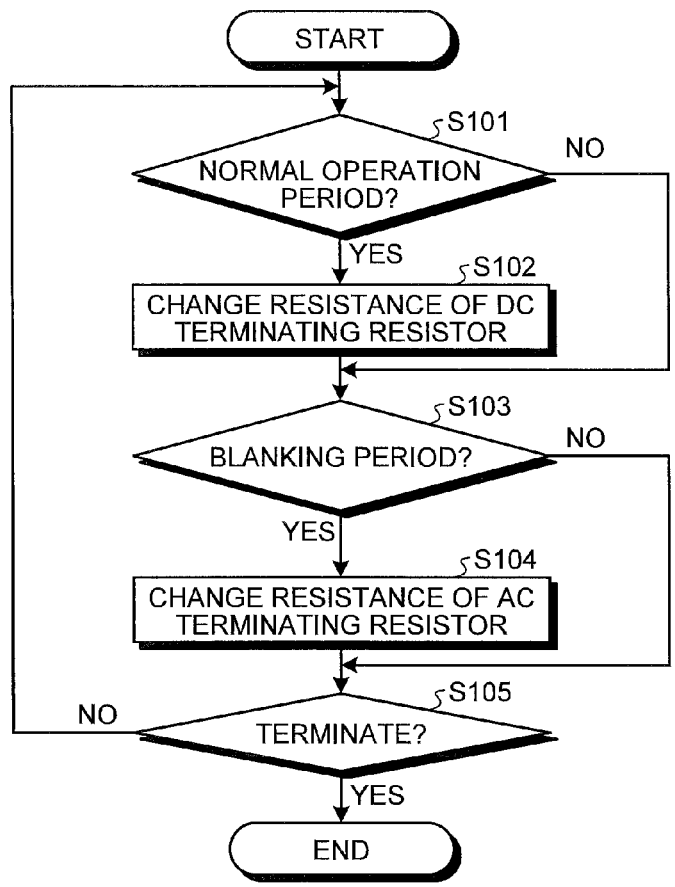
FIG. 4 is a table relating to a driving timing of each of a first switch of a DC terminating resistor and a second switch of an AC terminating resistor illustrated in FIG. 3 and a combined resistance of each of the DC terminating resistor and the AC terminating resistor.
FIG. 5 is a flowchart illustrating an outline of processing performed by an endoscope according to the first embodiment of the present invention.

FIG. 4 is a table T1 relating to a driving timing of each of the first switch 513 of the DC terminating resistor 501 and the second switch 523 of the AC terminating resistor 502 illustrated in FIG. 3 and the combined resistance of each of the DC terminating resistor 501 and the AC terminating resistor 502.

As illustrated in FIG. 4, during the blanking period of the imaging unit 20, the first switch 513 of the terminating resistor 51 is in an OFF state and the second switch 523 thereof is in an ON state under the control of the control unit 55. As a result, during the blanking period of the imaging unit 20, the DC terminating resistor 501 of the terminating resistor 51 has a resistance (200Ω) of only the first resistor 511, and the AC terminating resistor 502 thereof has a combined resistance (67Ω) of the third resistor 521 and the fourth resistor 522 since the third resistor 521 and the fourth resistor 522 of the AC terminating resistor 502 are in parallel. More specifically, in the terminating resistor 51, the DC terminating resistor 501 has a resistance during the blanking period of the imaging unit 20 higher than that in the normal operation period, and higher than the resistance of the AC terminating resistor 502 under the control of the control unit 55. As a result, the power consumption of the imaging unit 20 can be reduced.

Processing of Endoscope

Next, processing performed by the endoscope 2 will be described. FIG. 5 is a flowchart illustrating an outline of the processing performed by the endoscope 2.

As illustrated in FIG. 5, the control unit 55 determines whether or not the operation of the imaging unit 20 is in the normal operation period on the basis of a reference clock signal input from the clock generation unit 63 (step S101). If the control unit 55 has determined that the operation of the imaging unit 20 is in the normal operation period (step S101: Yes), the endoscope 2 proceeds to step S102.

Subsequently, the control unit 55 applies a voltage to the first switch 513 to change the resistance of the DC terminating resistor 501 (step S102). Specifically, the control unit 55 changes the resistance of the DC terminating resistor 501 to 100Ω.

Thereafter, the control unit 55 determines whether or not the operation of the imaging unit 20 is in the blanking period on the basis of a reference clock signal input from the clock generation unit 63 (step S103). If the control unit 55 has determined that the operation of the imaging unit 20 is in the blanking period (step S103: Yes), the endoscope 2 proceeds to step S104.

Subsequently, the control unit 55 applies a voltage to the second switch 523 to change the resistance of the AC terminating resistor 502 (step S104). Specifically, the control unit 55 changes the resistance of the AC terminating resistor 502 to 67Ω. As a result, during the blanking period in which no imaging signal is transmitted, the endoscope 2 can make the resistance of the DC terminating resistor 501 of the terminating resistor 51 higher than that of AC terminating resistor 502 so as to reduce current consumption.

Thereafter, if a termination signal to terminate the driving of the endoscope 2 is input from the input unit 9 (step S105: Yes), the endoscope 2 terminates the processing. If the termination signal to terminate the driving of the endoscope 2 is not input from the input unit 9 (step S105: No), the endoscope 2 returns to step S101.

If the control unit 55 has determined in step S101 that the operation of the imaging unit 20 is not in the normal operation period (step S101: No), the endoscope 2 proceeds to step S103.

If the control unit 55 has determined in step S103 that the operation of the imaging unit 20 is not in the blanking period (step S103: No), the endoscope 2 proceeds to step S105.

According to the first embodiment as described above, the control unit 55 makes the resistance of the DC terminating resistor 501 of the terminating resistor 51 during the blanking period of the imaging unit 20 higher than that of the terminating resistor 51 during the normal operation period. This can reduce power consumption of the imaging unit 20.

In addition, according to the first embodiment, since power consumption of the imaging unit 20 can be reduced, heat generation due to power consumed by the imaging unit 20 can be suppressed.

Furthermore, according to the first embodiment, since heat generation of the imaging unit 20 can be suppressed, the quality of a dark-time image can be improved.

Furthermore, according to the first embodiment, since heat generation of the imaging unit 20 can be suppressed, a saturated signal amount can be prevented from decreasing. As a result, a high-quality image can be obtained.

Furthermore, according to the first embodiment, since a mechanism for suppressing current need not be provided on the distal end side of the endoscope 2, the endoscope 2 can be made smaller.

Second Embodiment

Next, a second embodiment of the present invention will be described. An endoscope system according to the second embodiment has the same configuration as that of the endoscope system 1 according to the first embodiment described above, but differs therefrom in the configuration of the terminating resistor in the connector unit and in the processing of the endoscope. In the following, the configuration of the terminating resistor in the connector unit and the processing of the endoscope according to the second embodiment will thus be described. Note that the same components as in the endoscope system 1 according to the first embodiment described above will be designated by the same reference numerals, and the description thereof will not be repeated.

Configuration of Terminating Resistor

FIG. 6 is a circuit diagram illustrating a detailed configuration of the second chip 22 and a configuration of a main part of a connector unit 5a. As illustrated in FIG. 6, the connector unit 5a includes a terminating resistor 51a, an AFE unit 52, and an imaging signal processing unit 53.

The terminating resistor 51a includes a DC terminating resistor 501a, an AC terminating resistor 502a, and a DC blocking capacitor 503. The terminating resistor 51a has a constant combined resistance (50Ω) of the DC terminating resistor 501a and the AC terminating resistor 502a.

The DC terminating resistor 501a includes a fifth resistor 514 connected in parallel to the transmission cable 3 and a third switch 515 connected in series with the fifth resistor 514 in addition to the configuration of the DC terminating resistor 501 described above.

The fifth resistor 514 has one end connected to the third switch 515 and the other end connected to the ground. The fifth resistor 514 has a resistance of 600Ω.

The third switch 515 includes a NMOS, and has one end (drain side) connected to the transmission cable 3, the other side (source side) connected to the fifth resistor 514, and a gate to which a signal line for supplying a signal input from the control unit 55 is connected.

The AC terminating resistor 502a includes a sixth resistor 524 connected in parallel to the transmission cable 3 and a fourth switch 525 connected in series with the sixth resistor 524 in addition to the configuration of the AC terminating resistor 502 described above.

The sixth resistor 524 has one end connected to the fourth switch 525 and the other end connected to the ground. The sixth resistor 524 has a resistance of 300Ω.

The fourth switch 525 includes a NMOS, and has one end (drain side) connected to the transmission cable 3, the other side (source side) connected to the sixth resistor 524, and a gate to which a signal line for supplying a signal input from the control unit 55 is connected.

The thus configured terminating resistor 51a performs control to make the resistance of the DC terminating resistor 501a during the blanking period of the imaging unit 20 and during a high-gain operation period when a gain signal to increase the gain is input from the input unit 9 higher than that during the normal operation period under the control of the control unit 55. Furthermore, the terminating resistor 51a makes the resistance of the DC terminating resistor 501a higher than that of the AC terminating resistor 502a during the blanking period and the high-gain operation period under the control of the control unit 55.

FIG. 7 is a table T2 relating to a driving timing of each of the first switch 513 and the third switch 515 of the DC terminating resistor 501a and the second switch 523 and the fourth switch 525 of the AC terminating resistor 502a illustrated in FIG. 6 and a combined resistance of each of the DC terminating resistor 501a and the AC terminating resistor 502a.

As illustrated in FIG. 7, in the terminating resistor 51a during the high-gain operation period, the first switch 513 and the second switch 523 are in an OFF state while the third switch 515 and the fourth switch 525 are in an ON state under the control of the control unit 55. As a result, the terminating resistor 51a changes in the ratio of the resistance of the DC terminating resistor 501a to that of the AC terminating resistor 502a, and the resistance (150Ω) of the DC terminating resistor 501a becomes higher than the resistance (75Ω) of the AC terminating resistor 502a. Furthermore, in the terminating resistor 51a, the resistance of the DC terminating resistor 501a is made lower during the high-gain operation period than that during the blanking period. As a result, since the current consumption can be reduced during the high-gain period in which a saturation level is not used, the temperature at the imaging unit 20 (distal end portion) can be lowered and the image quality at a high gain can be improved. Furthermore, the terminating resistor 51a can reduce the power consumption of the imaging unit 20 during the blanking period similarly to the first embodiment described above.

Processing of Endoscope

Next, processing performed by the endoscope 2 will be described. FIG. 8 is a flowchart illustrating an outline of the processing performed by the endoscope 2.

In FIG. 8, steps S201 to S204 respectively correspond to steps S101 to S104 in FIG. 5 described above.

In step S205, if a gain signal to increase the gain is input from the input unit 9 (step S205: Yes), the control unit 55 applies voltages to the third switch 515 of the DC terminating resistor 501a and the fourth switch 525 of the AC terminating resistor 502a to perform control to change the ratio of the resistance of the DC terminating resistor 501a to the resistance of the AC terminating resistor 502a by changing the resistances of the DC terminating resistor 501a and the AC terminating resistor 502a (step S206). Specifically, the control unit 55 changes the resistance of the DC terminating resistor 501a to 150Ω and the resistance of the AC terminating resistor 502a to 75Ω. As a result, the endoscope 2 can reduce current consumption by making the resistance of the DC terminating resistor 501a higher than that of the AC terminating resistor 502a during the high-gain operation period (a period during which an area with a low brightness or a dark part is captured, for example) in which a saturation level is not used. After step S206, the endoscope 2 proceeds to step S207. Step S207 corresponds to step S105 in FIG. 5 described above.

If a gain signal to increase the gain is not input from the input unit 9 in step S205 (step S205: No), the endoscope 2 proceeds to step S207.

According to the second embodiment described above, in addition to the advantageous effects similar to those of the first embodiment described above, when a gain signal to increase the gain is input from the input unit 9, the control unit 55 applies voltages to the third switch 515 of the DC terminating resistor 501a and the fourth switch 525 of the AC terminating resistor 502a to perform control to change the ratio of the resistance of the DC terminating resistor 501a to the resistance of the AC terminating resistor 502a by changing the resistances of the DC terminating resistor 501a and the AC terminating resistor 502a. As a result, since the output voltage is normally lowered near saturation of the imaging signal output by the imaging unit 20, Vgs (in a case of a source follower buffer, for example) or VBE (in a case of an emitter follower, for example) cannot be sufficient, which disadvantageously deteriorate the linearity. During the high-gain period, however, a signal in a region in which the linearity is deteriorated is limited according to the input range of the AFE unit 52, which does not cause any problem even in high-load operation. As a result, since the current consumption can be reduced during the high-gain operation period in which a saturation level is not used, the temperature at the imaging unit 20 (distal end portion) can be lowered and the image quality at a high gain can be improved.

Third Embodiment

Next, a third embodiment of the present invention will be described. An endoscope system according to the third embodiment differs from the endoscope system 1 according to the second embodiment described above in the configurations of the second chip and the terminating resistor. In the following, the configurations of the second chip and the terminating resistor according to the third embodiment will thus be described. Note that the same components as in the endoscope system 1 according to the first embodiment described above will be designated by the same reference numerals, and the description thereof will not be repeated.

Configuration of Second Chip and Terminating Resistor

Figure 9:
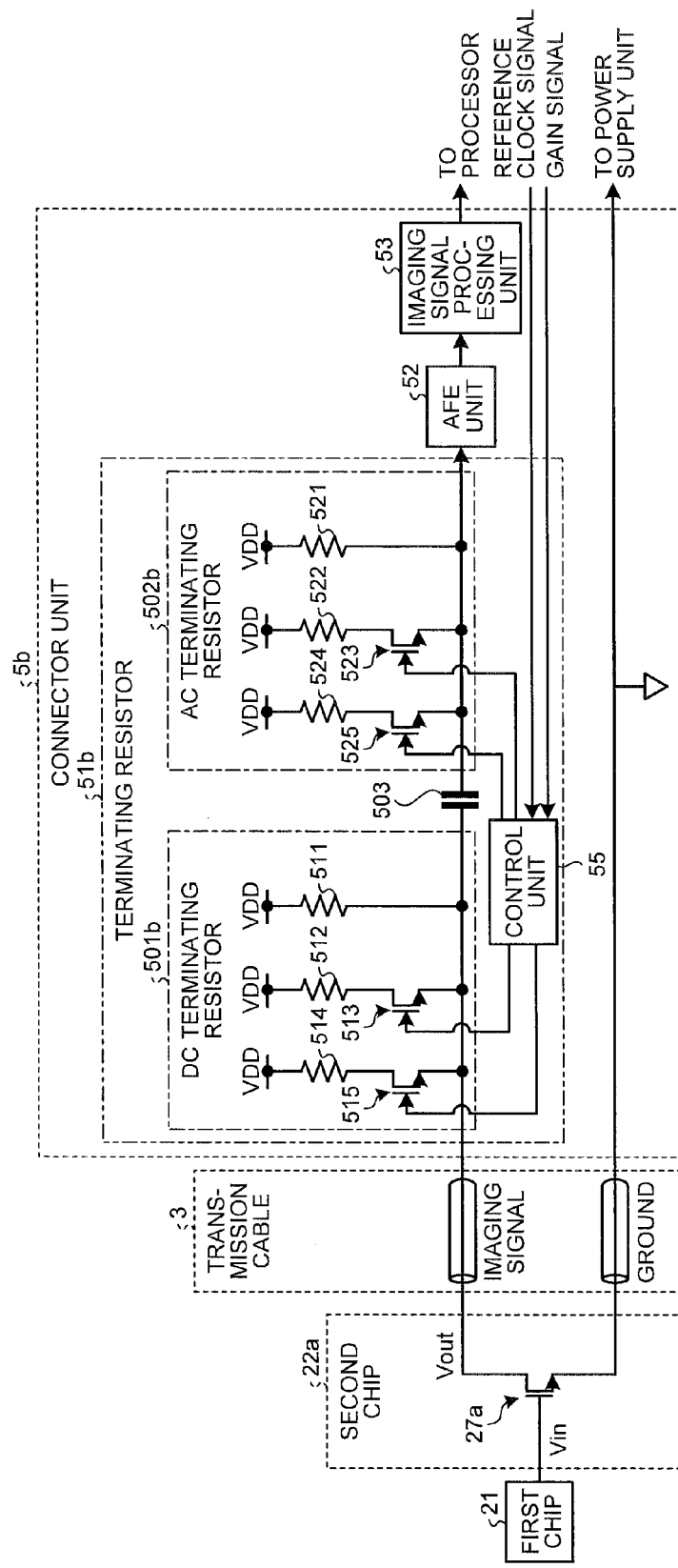
FIG. 9 is a circuit diagram illustrating a detailed configuration of a second chip and a configuration of a main part of a connector unit of an endoscope according to a third embodiment of the present invention.

FIG. 9 is a circuit diagram illustrating a detailed configuration of a second chip 22a and a configuration of a main part of a connector unit 5b. As illustrated in FIG. 9, the second chip 22a includes a buffer 27a configured to output an imaging signal output from the first chip 21.

The buffer 27a includes a NMOS, and has one end connected to the transmission cable 3, the other end connected to the ground, and a gate to which a signal line for supplying an imaging signal (Vin) input from the first chip 21 is connected.

The connector unit 5b includes a terminating resistor 51b, an AFE unit 52, and an imaging signal processing unit 53.

The terminating resistor 51b includes a DC terminating resistor 501b, an AC terminating resistor 502b, and a DC blocking capacitor 503. The terminating resistor 51b has a constant combined resistance (50Ω) of the DC terminating resistor 501b and the AC terminating resistor 502b.

The DC terminating resistor 501b includes a first resistor 511, a second resistor 512, a first switch 513, a fifth resistor 514, and a third switch 515. The first resistor 511, the second resistor 512, and the fifth resistor 514 are connected in parallel to the transmission cable 3.

The first resistor 511 has one end connected to the power supply voltage VDD and the other end connected to the transmission cable 3.

The second resistor 512 has one end connected to the power supply voltage VDD, and the other end connected in series with the first switch 513.

The first switch 513 has one end (drain side) connected to the second resistor 512, the other end (source side) connected to the transmission cable 3, and a gate to which a signal line for supplying a signal input from the control unit 55 is connected.

The fifth resistor 514 has one end connected to the power supply voltage VDD, and the other end connected in series with the third switch 515.

The third switch 515 has one end (drain side) connected to the fifth resistor 514, the other end (source side) connected to the transmission cable 3, and a gate to which a signal line for supplying a signal input from the control unit 55 is connected.

The AC terminating resistor 502b includes a third resistor 521, a fourth resistor 522, a second switch 523, a sixth resistor 524, and a fourth switch 525. The third resistor 521, the fourth resistor 522, and the sixth resistor 524 are connected in parallel to the transmission cable 3.

The third resistor 521 has one end connected to the power supply voltage VDD, and the other end connected to the transmission cable 3.

The fourth resistor 522 has one end connected to the power supply voltage VDD, and the other end connected in series with the second switch 523.

The second switch 523 has one end (drain side) connected to the fourth resistor 522, the other end (source side) connected to the transmission cable 3, and a gate to which a signal line for supplying a signal input from the control unit 55 is connected.

The sixth resistor 524 has one end connected to the power supply voltage VDD, and the other end connected in series with the fourth switch 525.

The fourth switch 525 has one end (drain side) connected to the sixth resistor 524, the other end (source side) connected to the transmission cable 3, and a gate to which a signal line for supplying a signal input from the control unit 55 is connected.

With the thus configured second chip 22a and connector unit 5b, the control unit 55 changes the resistance of the DC terminating resistor 501b by applying a voltage to the second switch 523 during the blanking period of the imaging unit 20 similarly to the second embodiment described above. Furthermore, the control unit 55 changes the resistance of the DC terminating resistor 501b to 150Ω and the resistance of the AC terminating resistor 502b to 75Ω during the high-gain operation period. As a result, the endoscope 2 can reduce current consumption by making the resistance of the DC terminating resistor 501b higher during the high-gain operation period in which a saturation level is not used.

According to the third embodiment described above, the same advantageous effects as those of the second embodiment are produced.

Modified Example

Figure 10:
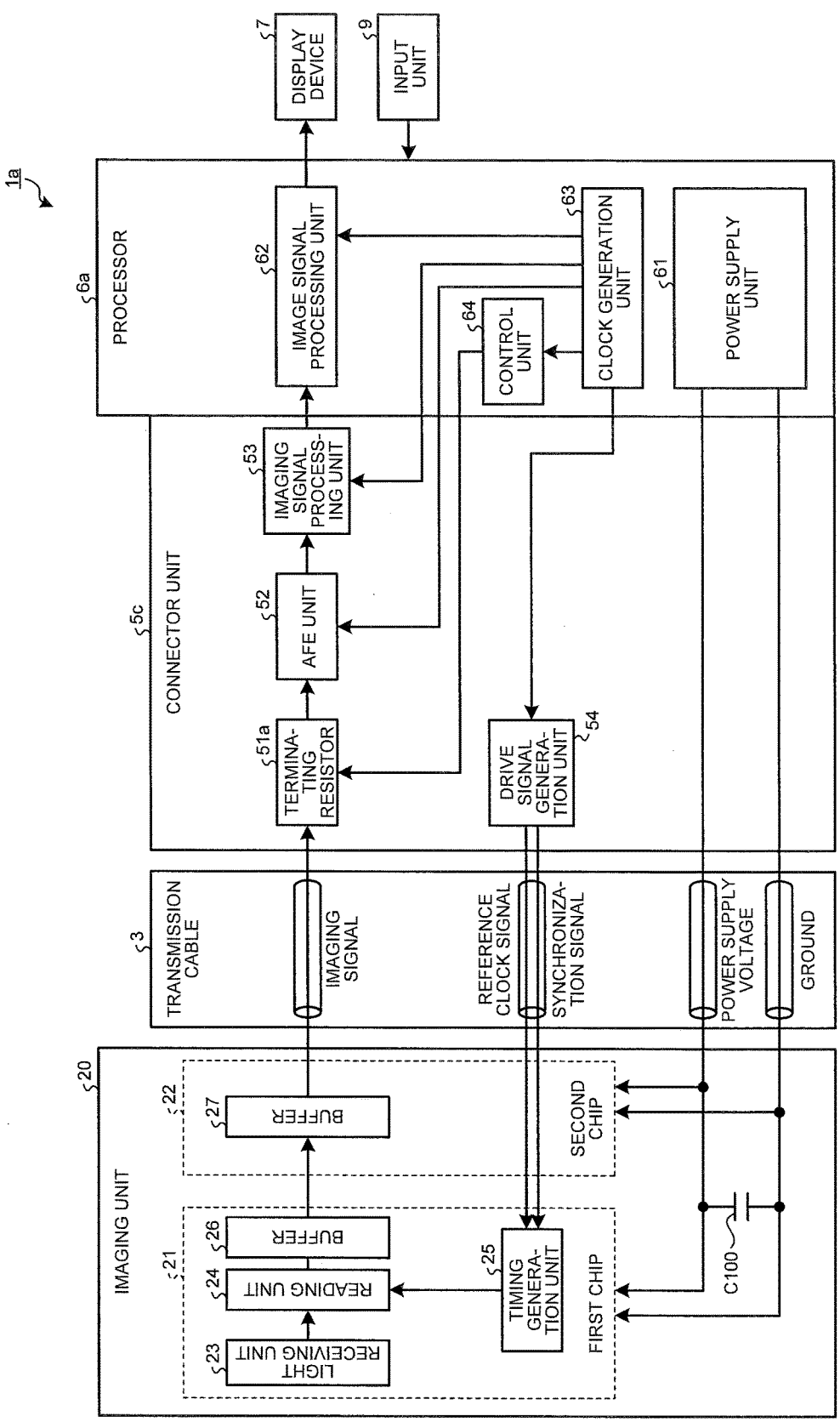
FIG. 10 is a block diagram illustrating functions of a main part of an endoscope system according to a modified example of the first to third embodiments of the present invention.

While the control unit is provided in the connector unit to perform control to change the resistance of the terminating resistor in the first to third embodiments described above, the control unit may alternatively be provided in the processor, for example. FIG. 10 is a block diagram illustrating a functional configuration of an endoscope system according to a modified example of the first to third embodiments.

As illustrated in FIG. 10, a connector unit 5c has the configuration of the connector units 5 to 5b according to the first to third embodiments described above except for the configuration of the control unit 55, and a processor 6a includes a control unit 64 in addition to the configuration of the processor 6 according to the first to third embodiments described above.

The control unit 64 performs control to change the resistance of the DC terminating resistor 501a of the terminating resistor 51a so as to suppress current of the endoscope 2 during the blanking period of the imaging unit 20 on the basis of the reference clock signal that is input from the clock generation unit 63 and that is a reference of operations of the respective components of an endoscope system 1a. Furthermore, if a gain signal to increase the gain is input from the input unit 9, the control unit 64 applies voltages to the third switch 515 of the DC terminating resistor 501a and the fourth switch 525 of the AC terminating resistor 502a to perform control to change the resistances of the DC terminating resistor 501a and the AC terminating resistor 502a. The control unit 64 includes a CPU (Central Processing Unit), for example.

According to the above-described modified example of the first to third embodiments, the same advantageous effects as those of the first to third embodiment are produced.

Other Embodiments

While the buffer is constituted by a NMOS in the embodiments described above, the buffer may alternatively include a PMOS, for example.

As described above, the present invention can include various other embodiments that are not described herein, and various modifications in designs and other modifications can be made within the scope of the technical idea defined by the claims.

According to the dosclosure, an advantageous effect of reducing power consumption can be produced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An imaging device comprising:
an image sensor including a plurality of pixels arranged in a two-dimensional matrix and configured to receive light from outside, and generate and output an imaging signal according to an amount of the received light;
a transmission cable connected to the image sensor and configured to propagate the imaging signal;
a terminating resistor provided at a terminal of the transmission cable, the terminating resistor including an alternating current terminating resistor with variable resistance and a direct current terminating resistor with variable resistance, and having a constant combined resistance of the direct current terminating resistor and the alternating current terminating resistor; and
a control unit configured to perform control to make a resistance of the direct current terminating resistor during a blanking period in which the image sensor does not output the imaging signal higher than that during a normal operation period in which the image sensor outputs the imaging signal.
2. The imaging device according to claim 1, wherein when an instruction signal indicating amplitude of the imaging signal is input from an external device, the control unit performs control to make a resistance of the direct current terminating resistor higher than the resistance during the normal operation period.
3. The imaging device according to claim 2, wherein the control unit performs control to make the resistance of the direct current terminating resistor during the blanking period higher than the resistance of the direct current terminating resistor when the instruction signal is input.

4. An endoscope comprising an imaging device comprising:
- an image sensor including a plurality of pixels arranged in a two-dimensional matrix and configured to receive light from outside, and generate and output an imaging signal according to an amount of the received light;
- a transmission cable connected to the image sensor and configured to propagate the imaging signal;
- a terminating resistor provided at a terminal of the transmission cable, the terminating resistor including an alternating current terminating resistor with variable resistance and a direct current terminating resistor with variable resistance, and having a constant combined resistance of the direct current terminating resistor and the alternating current terminating resistor; and
- a control unit configured to perform control to make a resistance of the direct current terminating resistor during a blanking period in which the image sensor does not output the imaging signal higher than that during a normal operation period in which the image sensor outputs the imaging signal.

5. An endoscope system comprising: an endoscope comprising:
- an image sensor including a plurality of pixels arranged in a two-dimensional matrix and configured to receive light from outside, and generate and output an imaging signal according to an amount of the received light;
- a transmission cable connected to the image sensor and configured to propagate the imaging signal;
- a terminating resistor provided at a terminal of the transmission cable, the terminating resistor including an alternating current terminating resistor with variable resistance and a direct current terminating resistor with variable resistance, and having a constant combined resistance of the direct current terminating resistor and the alternating current terminating resistor; and
- a control unit configured to perform control to make a resistance of the direct current terminating resistor during a blanking period in which the image sensor does not output the imaging signal higher than that during a normal operation period in which the image sensor outputs the imaging signal; and
- a processing device configured to convert the imaging signal to an image signal.

6. A method for driving an imaging device including:
an image sensor including a plurality of pixels arranged in a two-dimensional matrix and configured to receive light from outside, and generate and output an imaging signal according to an amount of the received light;
a transmission cable connected to the image sensor and configured to propagate the imaging signal; and
a terminating resistor provided with an alternating current terminating resistor with variable resistance and a direct current terminating resistor with variable resistance in parallel at a terminal of the transmission cable, and having a constant combined resistance of the direct current terminating resistor and the alternating current terminating resistor,
the method comprising:
performing control to make a resistance of the direct current terminating resistor during a blanking period in which the image sensor does not output the imaging signal higher than that during a normal operation period in which the image sensor outputs the imaging signal.

* * * * *